(12) United States Patent
Plunkett

(10) Patent No.: US 6,395,226 B1
(45) Date of Patent: May 28, 2002

(54) ALKOXYSILANE/ALKYSILANE COPOLYMER COATING OF MEDICAL DEVICES

(75) Inventor: Sean D. Plunkett, Mission Vie Jo, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/286,804

(22) Filed: Apr. 6, 1999

(51) Int. Cl.⁷ .................. A61M 1/14; A61M 37/00; C02F 1/44; B01D 53/22; B32B 5/02

(52) U.S. Cl. .................. 422/48; 422/44; 422/157; 604/6.09; 604/6.14; 210/645; 96/10; 261/DIG. 28

(58) Field of Search .............. 604/4.01, 6.09, 6.14; 422/44, 45, 48; 210/645–46, 650–54, 696, 767, 782, 348; 128/898; 424/400, 422–426, 486; 96/4, 7–11, 155, 218, 234, 235, 243, 296, 299; 428/391, 378, 446–47; 442/152–53, 157; 522/91, 99; 516/906; 556/400, 462; 435/289.1, 297.1–297.4; 261/296, 19, 28, 29, 75, DIG. 28

(56) References Cited

U.S. PATENT DOCUMENTS

| | | | |
|---|---|---|---|
| 3,846,359 A | * 11/1974 | Rostaing | |
| 4,049,873 A | * 9/1977 | Creasey et al. | |
| 4,906,465 A | * 3/1990 | Chaikof et al. | |
| 4,909,989 A | 3/1990 | Fukazawa et al. | ............. 422/48 |
| 4,923,679 A | * 5/1990 | Fukasawa et al. | |
| 5,643,681 A | 7/1997 | Voohees et al. | ............. 428/483 |
| 5,702,823 A | 12/1997 | Forrestal et al. | ............. 458/450 |
| 5,738,902 A | 4/1998 | Forrestal et al. | ............. 427/2.12 |
| 6,024,918 A | * 2/2000 | Hendriks et al. | |
| 6,136,938 A | * 10/2000 | Halloran | |

FOREIGN PATENT DOCUMENTS

| | | | |
|---|---|---|---|
| EP | 0353687 A2 | * 2/1990 | |
| WO | WO 91/15952 | 10/1991 | ............. A01N/1/00 |

* cited by examiner

Primary Examiner—Angela D. Sykes
Assistant Examiner—P M Bianco
(74) Attorney, Agent, or Firm—Thomas G. Berry; Stephen W. Bauer; Daniel W. Latham

(57) ABSTRACT

A coating for microporous hollow fiber membrane blood oxygenators increases the resistance of the fibers to passage of blood plasma through the micropores. The coating comprises alkoxysilane/alkylsilane copolymer, preferably aminoalkylsiloxane.

11 Claims, 10 Drawing Sheets

ALKOXYSILANE/ALKYSILANE COPOLYMER COATING OF MEDICAL DEVICES

TECHNICAL FIELD

This invention relates to medical devices, such as polyvinylchloride (PVC) tubing and oxygenators that use hollow fiber membranes to replace carbon dioxide in the blood with oxygen.

BACKGROUND

Microporous hollow fiber membrane oxygenators are commonly used to support patients during heart bypass procedures such as cardiac artery bypass grafting (CABG), heart valve repair and replacement, and the like. Such oxygenators are designed to direct blood flow over (or through) the microporous hollow fibers while oxygen-rich gas flows through (or over) the fiber lumens. This results in simultaneous mass transfer of molecular oxygen and carbon dioxide in opposite directions across the membrane.

The efficiency of the device can be described by the gas transfer per unit area of membrane at a given blood flow rate, gas flow rate, and composition (i.e., the specific gas transfer rate, typically cc of gas per liters of blood flow per minute per square meter of gas transfer area).

The micropores in the microporous hollow fibers are small enough to prevent whole-blood components such as platelets and red cells from passing through to the gas side of the membrane. However, the materials used to manufacture the fiber (polypropylenes, polyethylenes) are not primarily designed for blood compatibility. Both platelets and leukocytes adhere in great numbers to the materials, leading to significant activation of deleterious responses in the blood.

Several coating methods have been used to improve blood compatibility by providing an additional layer or "second skin" for the underlying structural material comprising the fiber membrane. The added layer of material provides a blood-surface interaction superior to that seen for the bulk fiber materials. For example, heparin is known to have good blood compatibility properties and has been used as a coating on several commercialized products. Unfortunately, heparin-based coatings are inherently expensive and complex due to the use of sodium heparin, a complex, costly and fragile biologically derived substance.

The Carmeda Bioactive Surface (Medtronic, Inc.) uses a polymer primer coat followed by covalent attachment of heparin to primary amino groups present in the primer coat. The Duraflo Bonded Heparin Surface (Baxter, Inc.) uses a heparin-polymer blend-based coating that is intended to achieve similar results. Other heparin-based coatings intended to improve blood compatibility are available from other medical device manufacturers (Terumo, Jostra, 3M Sarns, etc.).

Silicone (polydimethyl siloxane-based resins) is known to be compatible with blood. A process commercialized by Cobe Laboratories, Inc. uses a block copolymer polymer additive/coating that is intended to decrease platelet and leukocyte adhesion/activation.

Another problem is that, over time, the fluid component of blood (plasma) can migrate through the pores, a problem known as plasma migration or plasma breakthrough. In the case of a design in which the blood flows over the fibers and the oxygen-rich gas flows within the fiber lumens, this migration will eventually render the device inoperable by filing the lumens with liquid that impedes gas flow.

Reducing the average pore size can increase the time to failure somewhat. This is the approach taken in a fiber commercially available from Hoescht-Celanese and known under the tradename of Plasma Resistant Fiber or PRF. Further improvement is desireable.

One approach to the problem has been to use nonporous silicone membrane oxygenation systems. While no plasma can migrate through the membrane, gas transfer is very poor compared to that of microporous hollow fiber membrane oxygenators due to gas diffusion limitations through the solid polymer material.

Another approach to improving plasma breakthrough performance is to modify the microporous hollow fiber membrane. Previous coating methods have attempted to close off the pores with a thin film of silicon resin, mechanically preventing fluid migration. Specific gas transfer rates are improved compared to silicon membrane oxygenators, but are still well below the rates found in uncoated microporous hollow fiber membrane devices.

Another approach is the use of chemical vapor deposition (CVD) to deposit various coatings such as silicone resins on devices (e.g., Thoratec, InnerDyne). This approach suffers from poor specific gas transfer and also uses costly, toxic reagents. In addition, the CVD method is difficult to apply to the internal surfaces of finished products.

Biocompatibles, Inc. has a process for applying a phosphatidyl choline-methacrylate/butyl methacrylate copolymer that is intended to improve blood compatibility. BioInteractions, Inc. has a hydrogel/heparin mixture that is also intended to improve blood compatibility of blood oxygenators.

SUMMARY OF THE INVENTION

The invention is a method of coating a medical device, and the coated medical device itself. The device may be polyvinylchloride (PVC) tubing, any device comprising microporous hollow fiber membranes (such as blood oxygenators), or any other medical device which is prone to the plasma migration or plasma breakthrough problem.

The coating compound of the invention comprises alkoxysilane/alkylsilane copolymers, preferably aminoalkylsiloxane, and most preferably the aminoalkylsiloxane sold under the trade designation of MDX4-4159, commercially available from Dow Corning (see, for example, the URL at www.factor2.com/a-4159.htm).

One of the key aspects of this process is that it uses a siloxane material that cures in-place under very mild conditions. This is due to the use of an alkoxysilane/alkylsilane copolymer as mentioned above. The material cures via crosslinking of the alkoxysilane groups with each other, which occurs at room temperature in the presence of a trace of water as catalyst.

The method of coating the medical device creates a thin film of silicone on the device (including the microporous fibers of the device), but does not cover or fill the micropores with the thin film. The improved resistance to plasma breakthrough (i.e., increased time to device failure) is achieved instead by changing the surface of the fiber polymer near the pore opening to better resist the intrusion of plasma. The prepolymer is applied as a thin film via solvent; after the solvent carrier evaporates away, the prepolymer cures to a soft resin layer completely covering the treated surface. All blood contact occurs with the silicon resin rather than with the underlying material.

The result is a device with significantly greater time to failure for plasma breakthrough with specific gas transfer rates almost unchanged compared to identical uncoated devices. The process is also economically attractive, easier to implement, avoids toxic reagents, and can be used with a wider variety of finished products.

DETAILED DESCRIPTION

Figure 1:
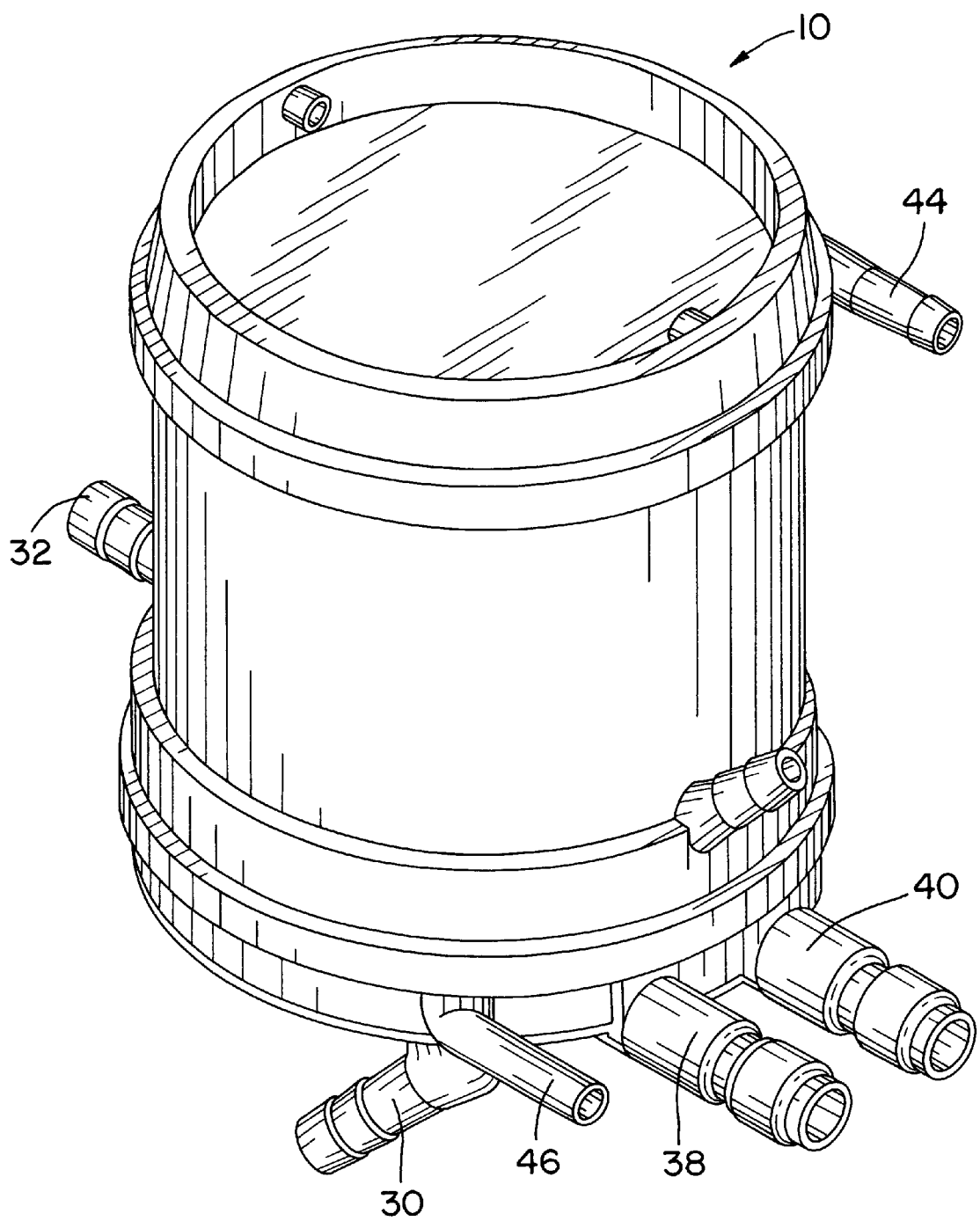
FIG. 1 is a perspective view of a blood oxygenator constructed in accordance with this invention.
Figure 2:
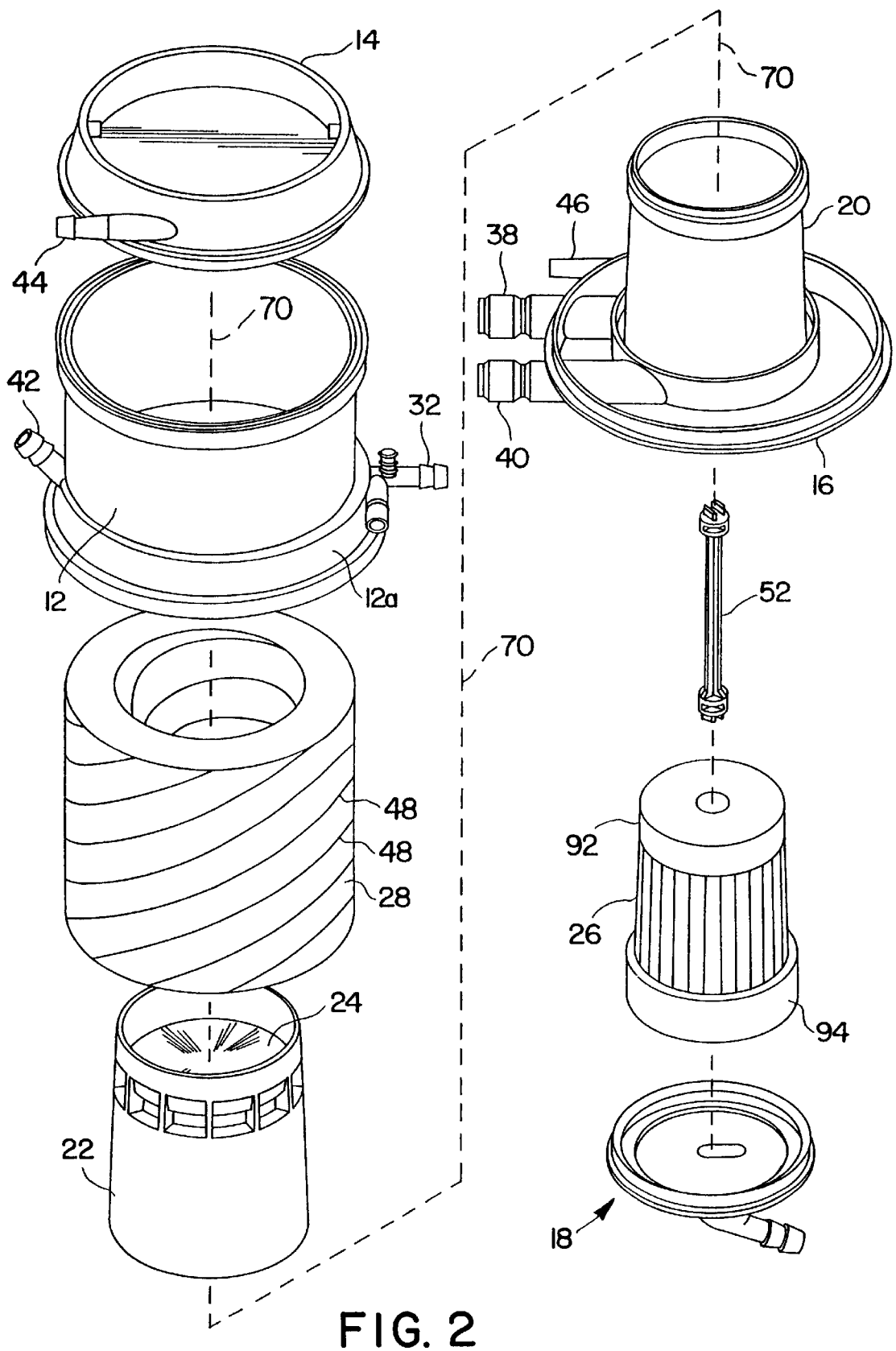
FIG. 2 is an exploded isometric view of a blood oxygenator constructed in accordance with this invention.

Commercially available examples of oxygenators employing microporous hollow fiber membranes for blood/gas exchange include those sold under the trade designation of AFFINITY and MAXIMA FORTÉ, available from Medtronic Perfusion Systems, Medtronic, Inc. of Minneapolis, Minn., USA. See U.S. Pat. No. Re. 36,125, U.S. Pat. Nos. 5,462,619, and 5,346,621 for the trade designation AFFINITY brand oxygenator; and U.S. Pat. Nos. 5,858,233, 5,823,987, 5,762,875, and 5,718,871 for the trade designation MAXIMA FORTÉ brand oxygenator. All of these patents are entirely incorporated by reference into this document.

The aminoalkylsiloxane having the trade designation MDX4-4159 (Dow Corning). Fluid 50% Medical Grade Dispersion is sold as a liquid RTV solution containing 50 percent active silicone ingredients in mixed aliphatic and isopropanol solvents. The active silicone used is an aminofunctional dimethylsiloxane copolymer. The polar nature of the aminofunctional groups and the ability of the fluid to cure cause films to deposit and adhere to metal cutting edges, such as razor blades. The primary known use of the aminoalkylsiloxane having the trade designation MDX4-4159 is dipping, coating and spraying devices to create a thin layer of silicone for lubrication.

The most general expression of the alkoxysilane/alkylsilane copolymer coating of the invention is a random or block coploymer of the form:

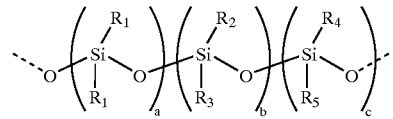

Where:
$R_1$=alkyl group, preferably —$CH_3$ methyl
$R_2$=alkoxy group such as —O—$CH_3$ or —O—$CH_2CH_3$
$R_3$=alkyl or alkoxy side chain as above
$R_4$=a functional group such as —$CH_2CH_2CH_2NHCH_2CH_2NH_2$ (preferred, but not limited to this)
$R_5$=Functional group, alkoxy group or alkyl group
$a>>b$ and $a>>c$ A preferred embodiment of the invention may be illustrated by considering the design of the oxygenator sold under the trade designation of MAXIMA FORTÉ, available from Medtronic Perfusion Systems, Medtronic, Inc., Minneapolis, Minn., USA. Of course, details described below that are specific to this device, but not necessary to practice of the invention, may be different in other embodiments of the invention.

Referring to FIGS. 1–4, a blood oxygenator 10 comprises an outer generally cylindrical vessel 12, which is sealed at its upper end by a generally saucer-shaped upper hollow venous gas header 14. A generally saucer-shaped lower hollow venous gas header 16 seals the lower end of the vessel 12. A blood inlet manifold 18 is connected to the: center of the underside of the lower venous gas header 16. Concentric, generally cylindrical inner and outer heat exchanger housings 20 and 22 are connected at their lower ends to the center of the lower venous header 16. The upper end of the outer heat exchanger housing 22 includes a transition manifold 24. The interior of the inner heat exchanger housing 20 surrounds and encloses a generally cylindrical first fiber bundle 26 made up of a plurality of vertically oriented hollow micro-conduits. These micro-conduits convey blood vertically upward. A second generally cylindrical fiber bundle 28 concentrically surrounds the outer heat exchanger housing 22 and is positioned inside the inner wall of the cylindrical vessel 12. The upper and lower ends of the generally ring-shaped second fiber bundle 28 interact with the upper and lower venous gas headers 14 and 16, respectively.

The blood inlet manifold 18 (FIG. 3) includes a barbed blood inlet nozzle 30 which bends downwardly at an angle relative to the central vertical axis of the vessel 12. A barbed blood outlet nozzle 32 (FIGS. 3 and 4) extends horizontally from the exterior of an enlarged or flared portion 12a of the vessel 12. A standard Leur fitting 34 (FIG. 3) extends vertically from the base of the blood outlet nozzle 32. A thermometer probe fitting 36 (FIG. 4) extends horizontally from the base of the blood outlet nozzle 32.

Inlet and outlet nozzles 38 and 40 (FIGS. 2 and 4) for a heat transfer fluid such as water extend horizontally from one side of the low venous gas header 16 and communicate with water flow passages inside the inner heat exchanger housing 20. A barbed de-bubbler nozzle 42 (FIG. 3) extends upwardly at an angle from the flared portion 12a of the vessel 12. A gas mixture inlet nozzle 44 (FIGS. 2, 3 and 4) extends horizontally from the periphery of the upper venous gas header 14. A gas mixture outlet nozzle 46 (FIGS. 2 and 4) extends from the periphery of the lower venous gas header 16 parallel to the water inlet and outlet nozzles 38 and 40.

Figure 5:
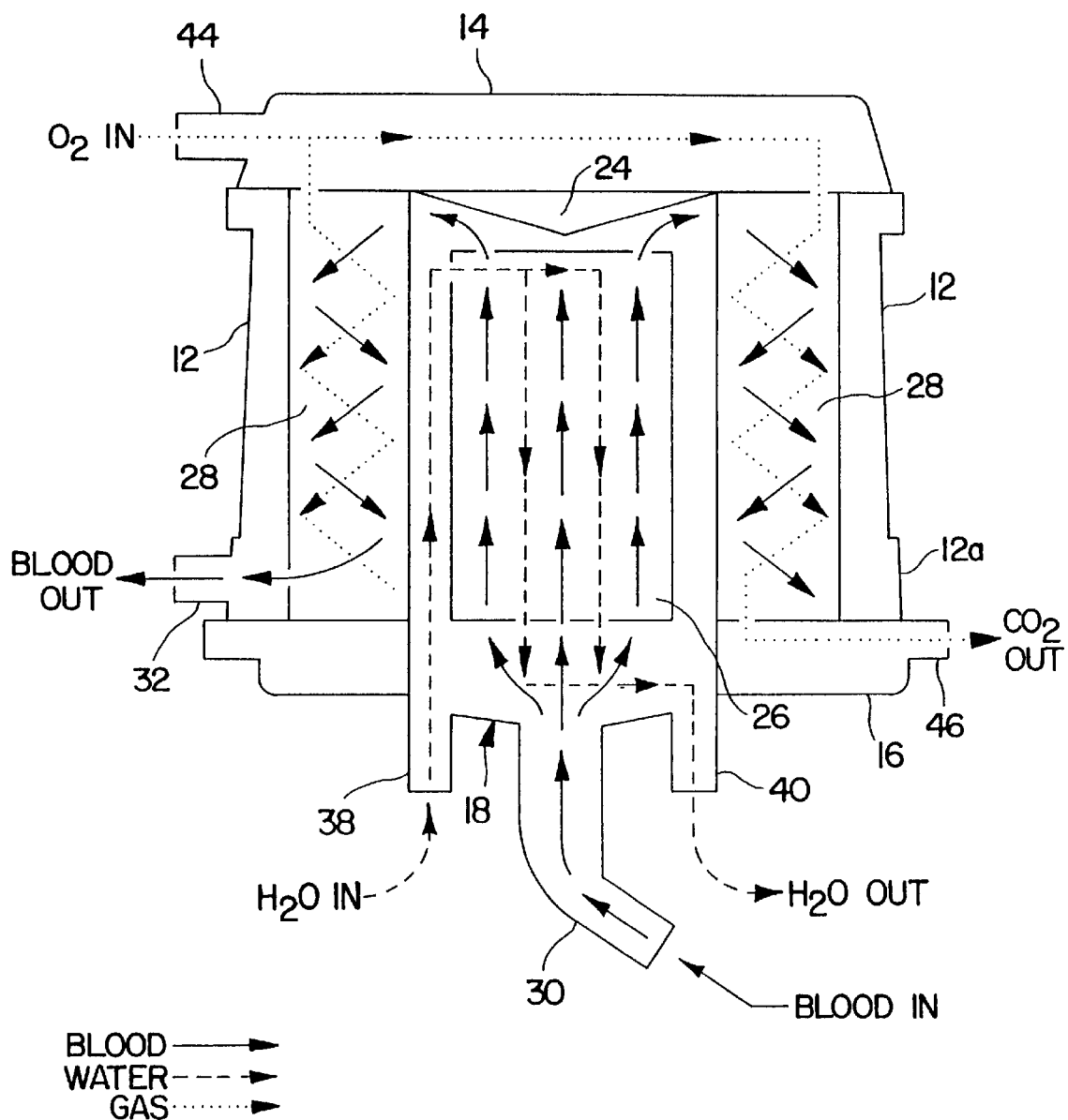
FIG. 5 is a diagrammatic view illustrating the blood, heat transfer fluid and gas mixture flow paths of the blood oxygenator of FIGS. 2–4.
Figure 6:
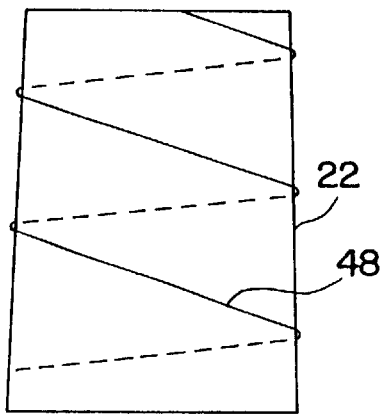
FIG. 6 is a diagrammatic view illustrating the fabrication of the oxygenator fiber bundle of the blood oxygenator of FIGS. 2–5.

The blood, heat transfer fluid and gas mixture flow paths of the blood oxygenator 10 can best be understood by way of reference to the diagrammatic vertical sectional view of FIG. 5. In that figure, the flow of blood is illustrated diagrammatically by the bold solid arrows. The dashed lines illustrate the flow of heat transfer fluid (water). The flow of gas mixture is illustrated by the sequence of dots. Blood from the patient flows through tubing (not illustrated) connected to the blood inlet nozzle 30. This incoming blood spreads out through the blood inlet manifold 18 and travels vertically through the micro-conduits of the first fiber bundle 26 of the central heat exchanger that forms the core of the blood oxygenator 10. Water flows in through the inlet nozzle 38 vertically to the top of the heat exchanger fiber bundle 26 through a separate channel isolated from the fiber bundle 26. The water is then directed down and across the outside of the micro-conduits of the fiber bundle 26. The water flows around the outside of the micro-conduits opposite the flow of the blood within the micro-conduits. The water exiting from the lower end of the first fiber bundle 26 exits through the outlet nozzle 40.

The water is heated or cooled outside the blood oxygenator, as necessary to regulate the temperature of the blood flowing through the micro-conduits of the heat exchanger. The use of a counter-flow heat exchanger provides optimum heat exchange efficiency. However, as noted above, the counter-flow design is not essential to the invention.

Figure 3:
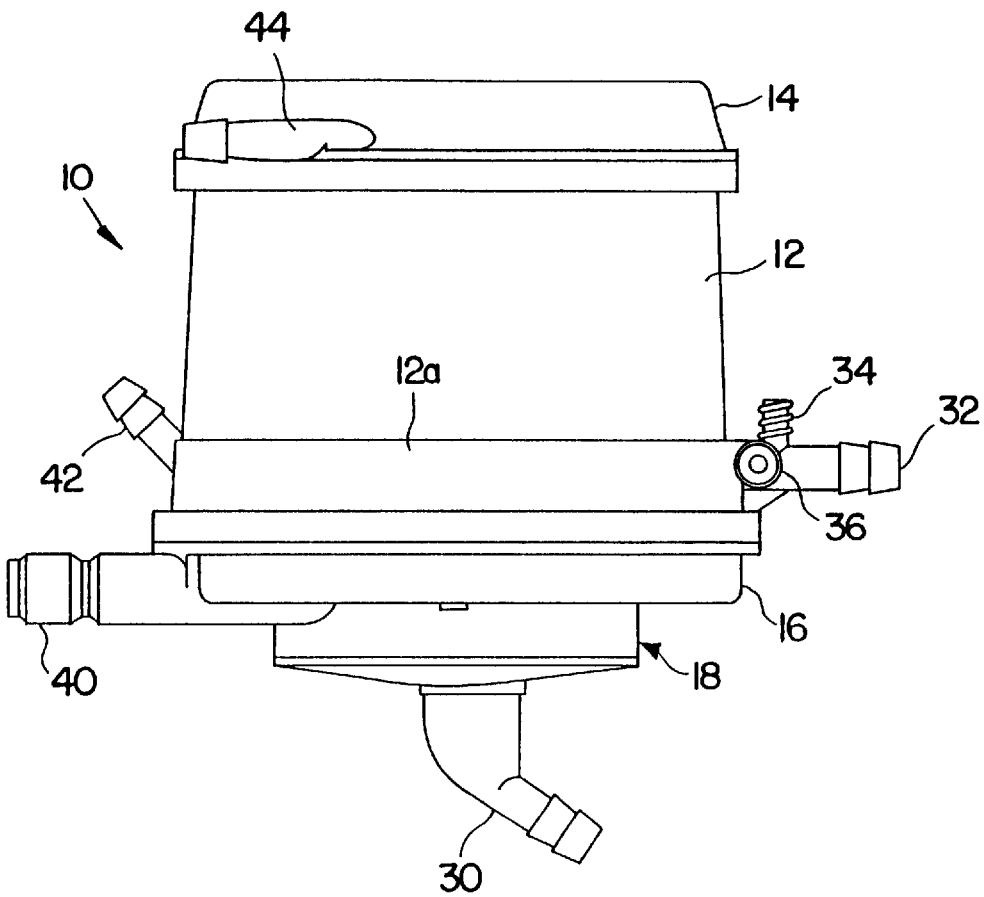
FIG. 3 is a side elevation view of the assembled blood oxygenator of FIG. 2.
Figure 4:
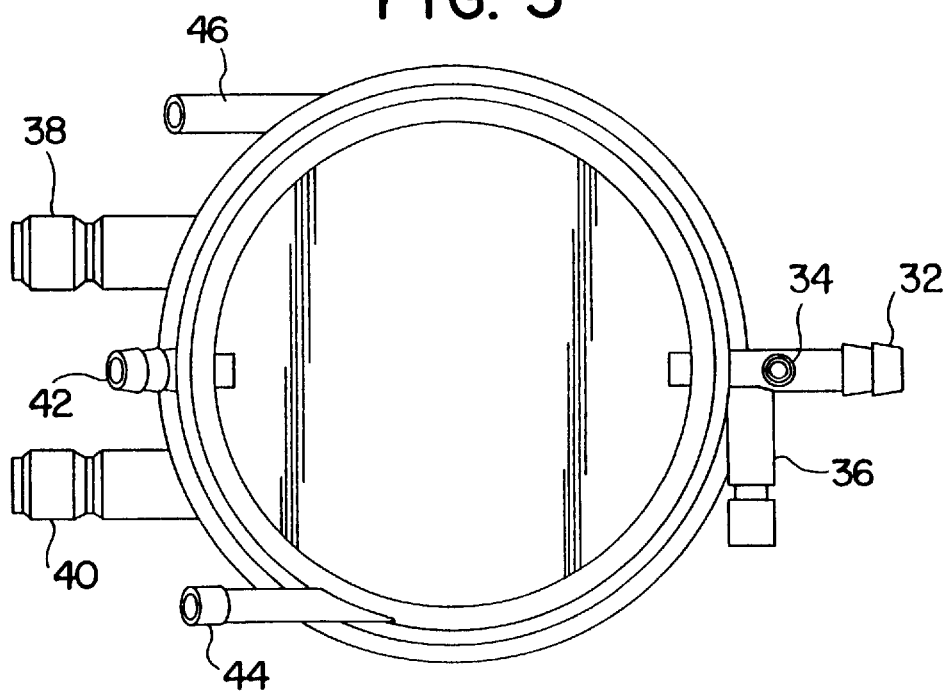
FIG. 4 is a top plan view of the blood oxygenator of FIG. 3.

The temperature of the blood can be monitored by a circuit (not illustrated) that includes a thermistor or other temperature sensing device (not illustrated) mounted inside the thermometer probe fitting 36 (FIGS. 3 and 4). The thermometer probe fitting 36 is a preferred location for connection of an electrical bridge to the blood side of the heat exchanger, since the temperature sensing device is likely to be coincidentally an electrically conductive material (typically metal) already in physical contact with the blood. Thus, the invention may be implemented by connecting a conductive bridge between the temperature sensing device and any convenient location on the other side of the heat exchanger.

Blood exiting from the upper end of the first fiber bundle 26 (FIG. 5) of the heat exchanger is directed radially outwardly by the transition manifold 24. This blood then travels around the outside of the fibers of the second fiber bundle 28 that forms the oxygenator. The blood travels downwardly past the outside surfaces of the fibers of the second fiber bundle 28. When the blood reaches the lower portion of the second fiber bundle 28, it is collected in an outlet manifold defined by the flared portion 12a of the vessel and exits through the blood outlet nozzle 32. The blood outlet nozzle 32 is connected to tubing (not illustrated) for returning the blood to the patient.

A gas mixture rich in oxygen from a pressurized source (not illustrated) is conveyed through a hose (not illustrated), through the gas mixture inlet nozzle 44, and into the upper venous gas header 14. The upper gas header 14 communicates with the upper ends of the fibers in the second fiber bundle 28 forming the membrane oxygenator. The oxygen-rich gas mixture travels down through the interior of the fibers in the fiber bundle 28. These fibers are micro-porous. Carbon dioxide from the blood surrounding the fibers in the bundle 28 diffuses through the walls of the fibers into the gas mixture. Similarly, oxygen from the gas mixture inside the fibers of the bundle 28 diffuses through the micro-pores into the blood. The gas mixture now having an elevated carbon dioxide content exits the lower ends of the fibers of the second fiber bundle 28 into the lower venous gas header 16 and then exits therefrom via the gas mixture outlet nozzle 46. This gas mixture now has a lower oxygen content. The nozzle 46 is connected to another gas hose (not illustrated).

Figure 7:
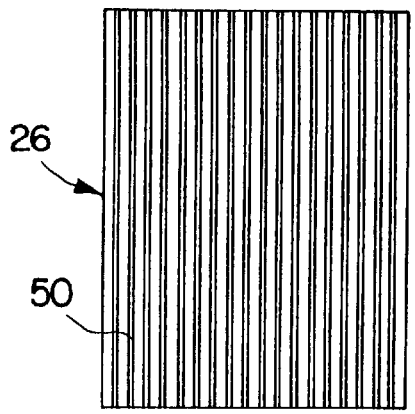
FIG. 7 is a diagrammatic view of the heat exchanger fiber bundle of the blood oxygenator of FIGS. 2–5.

FIG. 7 is a diagrammatic illustration of the first fiber bundle 26 which serves as the core of the heat exchanger portion of the blood oxygenator 10. The fiber bundle 26 has a generally cylindrical configuration and comprises approximately five thousand four hundred vertically (axially) extending hollow fibers 50. Preferably the fibers are provided as a continuous long web of micro-conduit wrapping material in which the fibers are held together by a thin, flexible, horizontally extending woven interconnect. Such wrapping material is commercially available from Mitsubishi Rayon, Co., Ltd. under the trade designation HFE430-1 Hollow Fiber. This material uses polyethylene fibers. Similar wrapping material is also commercially available from Hoechst Celanese Corporation under the designation Heat Exchanger Fiber Mat. This material uses polypropylene fibers.

Figure 8:
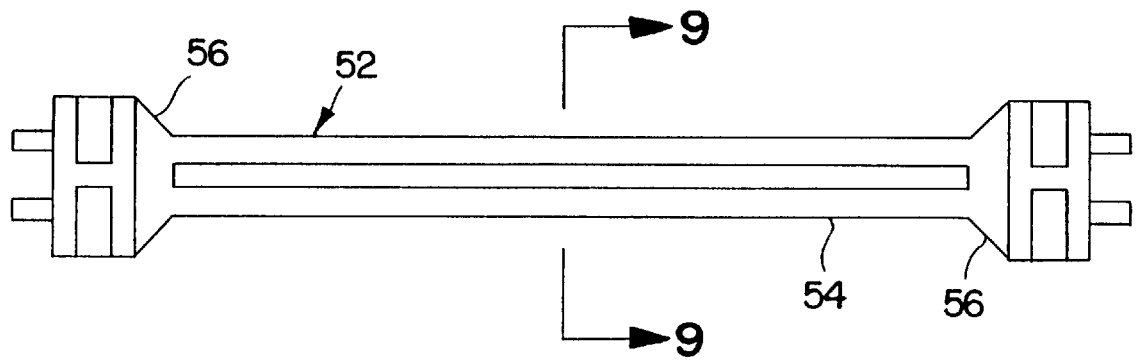
FIG. 8 is an enlarged side elevation view of the spindle of the heat exchanger of the blood oxygenator around which is wound the micro-conduit wrapping material.
Figure 9:
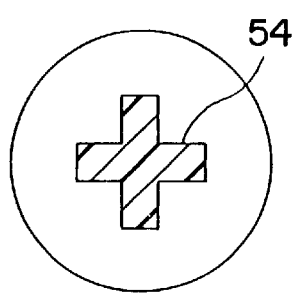
FIG. 9 is a cross-section view of the spindle of FIG. 8 taken along line 9—9 of FIG. 8.
Figure 10:
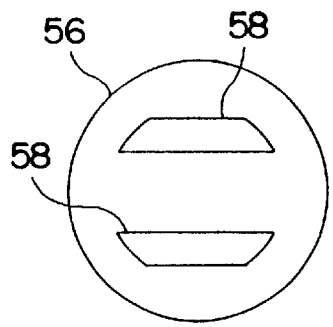
FIG. 10 is an end elevation view of the spindle of FIG. 8 taken from the right end of FIG. 8.

The micro-conduit wrapping material of the heat exchanger core is wound about a central, vertically orientated elongated spindle 52 (FIG. 8). The spindle 52 has an intermediate segment 54 having a cross-shaped cross-section, as best seen in FIG. 9. The spindle 52 has enlarged driving ends 56 connected to the opposite ends of the intermediate segment 54. Each of the driving ends 56 has a pair of parallel extending ribs 58 (FIG. 10) which are used to lock the spindle into a winding machine (not illustrated). This machine utilized to wind the micro-conduit wrapping material about the spindle 52. Preferably the micro-conduit wrapping material is compactly wound about the central spindle 52, but without any substantial tension on the web.

As mentioned above, the micro-conduit may be provided in a heat exchanger micro-conduit wrapping material. The wrapping material comprises micro-conduit fibers attached to a thin flexible interconnect, such as woven netting, to maintain the fibers at predetermined spacings in substantially parallel alignment with each other. The wrapping material is wrapped about an elongated spindle having first and second ends, such that the ends of each fiber reside proximate the spindle's first and second ends. After the ends of the fibers are trimmed as needed, a shell is placed around the wrapping material and spindle. Opposing first and second seals are created by applying potting compound between fibers proximate the spindle's first end and proximate the spindle's second end.

Figure 11:
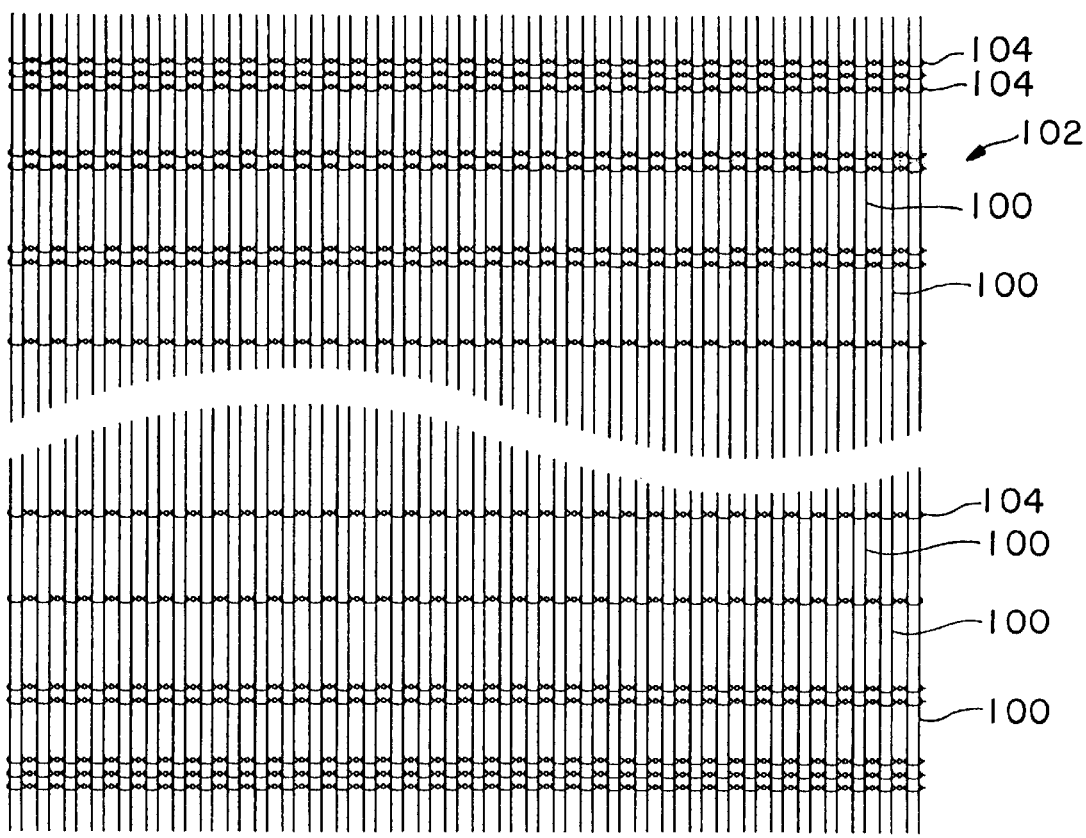
FIG. 11 is a side detail view of polymeric micro-conduit material suitable for construction of the bundle of FIG. 7.
Figure 12:
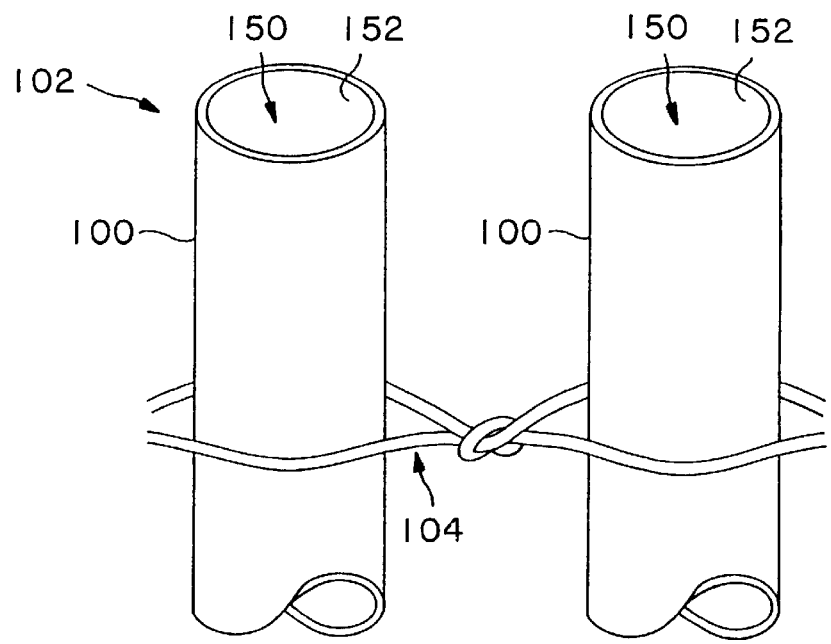
FIG. 12 is a magnified side detail view of a portion of the polymeric micro-conduit material of FIG. 11.
Figure 13:
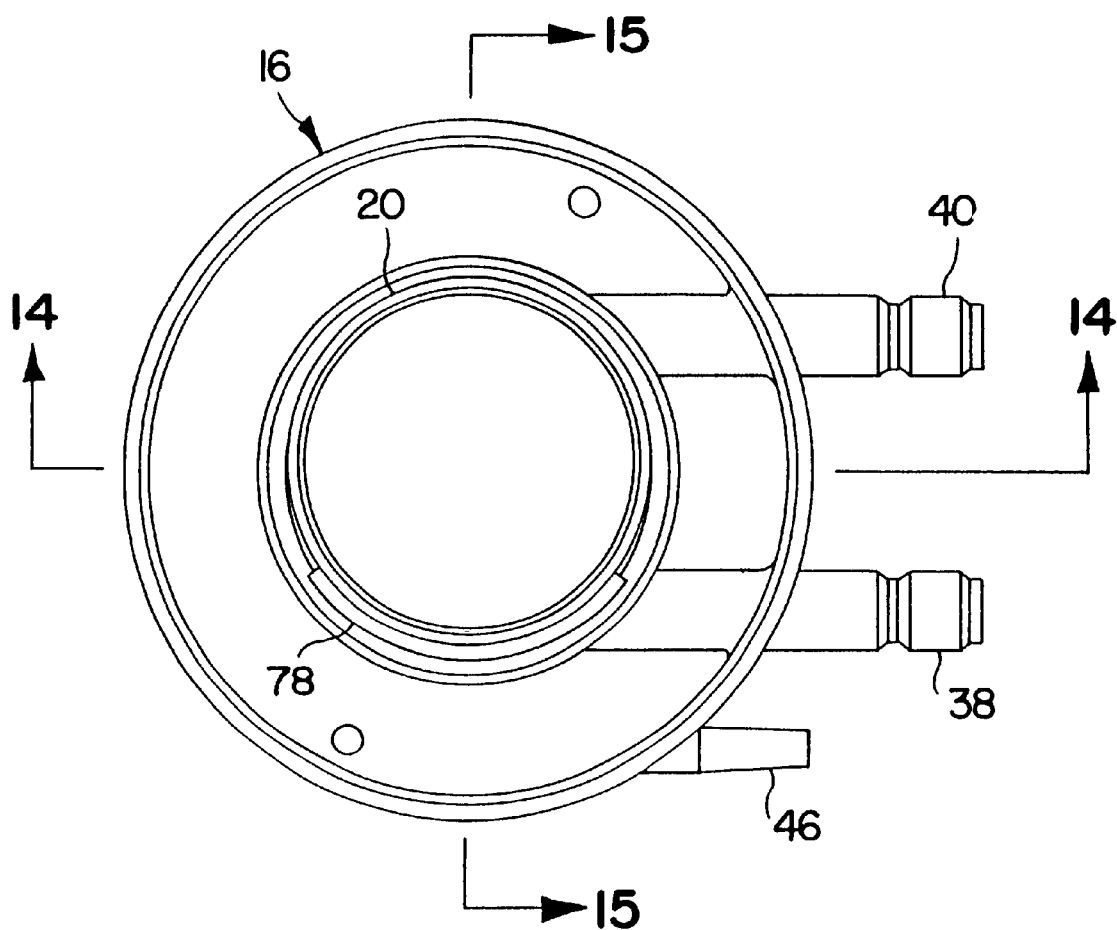
FIG. 13 is a top plan view of the lower venous gas header of the blood oxygenator. Also visible in this figure are the inner heat exchanger housing, the water inlet nozzle, the water outlet nozzle and the gas mixture outlet nozzle.
Figure 14:
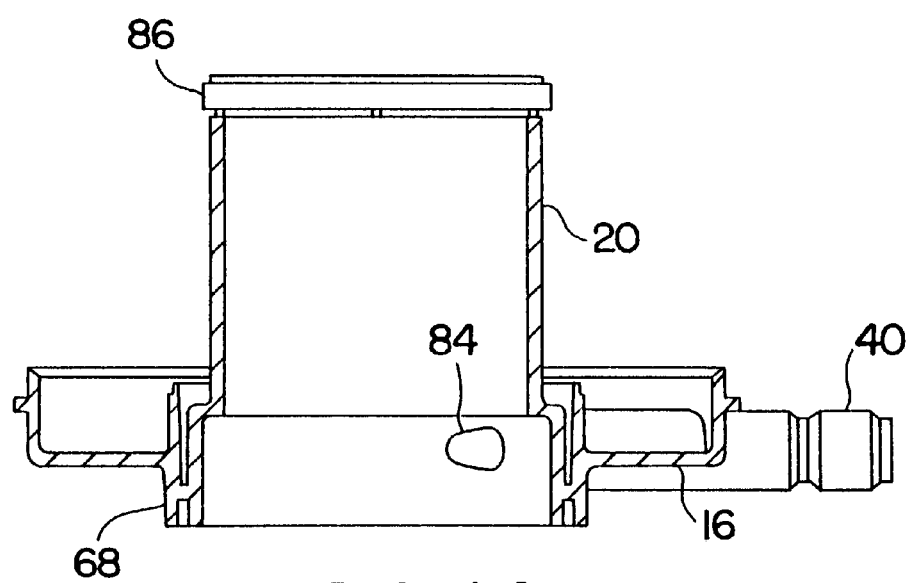
FIG. 14 is a sectional view of the lower venous gas header and inner heat exchanger housing taken along line 14—14 of FIG. 13.
Figure 15:
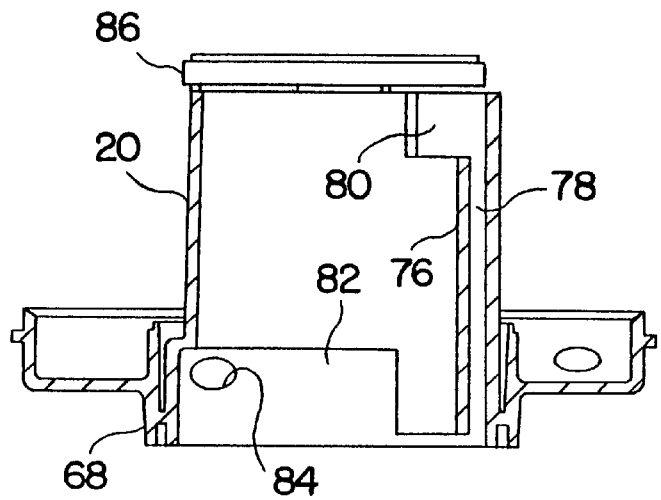
FIG. 15 is a sectional view of the lower venous gas header and inner heat exchanger housing taken along line 15—15 of FIG. 13.
Figure 16:
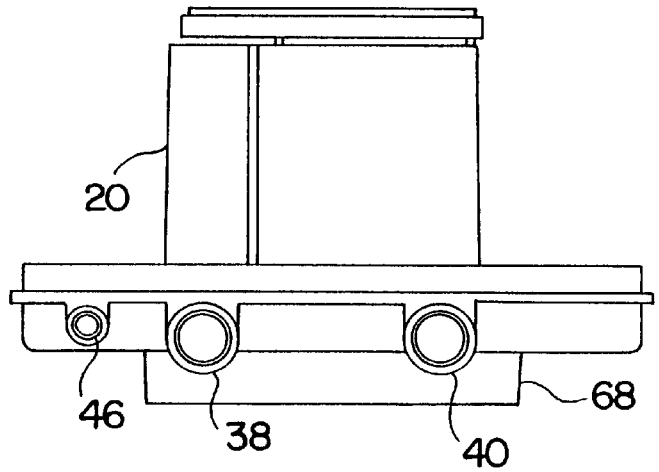
FIG. 16 is a front elevation view of the lower venous gas header and inner heat exchanger housing of the blood oxygenator.

A shown in detail in FIGS. 11 and 12, the heat exchanger micro-conduit, "micro-conduit" for short, preferably comprises a plurality of small fibers 100, as shown in FIG. 11. In FIG. 11, the fibers 100 are arranged in a "mat" of micro-conduit wrapping material 102, which is described in greater detail below. Each fiber 100 comprises an elongated two-ended fiber. Each fiber 100 is hollow, with a cross-sectional shape preferably being rounded, or alternatively triangular, rectangular, or another appropriate shape. Since the fibers 100 are hollow, each fiber 100 defines an inner channel 150 having an inner surface 152, as shown in FIG. 12. In the illustrated embodiment, the outer diameter of the fiber is about four hundred and seventy-five microns while the diameter of the inner channel 150 is about four hundred and twenty-eight microns. However, a wide variety of inner and outer diameters may be used, depending upon the requirements of the particular application. The difference between the inner and outer diameters is preferably small, to encourage heat exchange through the fibers' walls. The fibers 100 may be about ten centimeters long, for example. However, a wide range of fiber lengths may be used, depending upon the requirements of the particular application.

The fibers 100 may be made from a plastic material such as polypropylene, polyethylene, a different polymeric substance, or another material that is inexpensive, pharmacologically safe, lightweight, easily cut, and flexible. The material of the fibers 100 must also be easily formed into fibers with sufficiently small inner and outer dimensions. Preferably the fibers 100 would be made of a hydrophilic material, however, micro-conduit made of such material is not presently commercially available.

As mentioned above, FIG. 11 illustrates a section of micro-conduit wrapping material 102. The material 102 includes a thin flexible interconnect 104 that maintains the fibers 100 at predetermined spacings in substantially parallel alignment with each other. In the illustrated embodiment, the interconnect comprises substantially parallel lengths of flexible thread that are woven or knotted to hold the fibers about 0.5 mm apart, generally parallel to each other. The wrapping material 102 aids in positioning the fibers 100 during construction of a blood heat exchanger, as discussed below.

The mat or wrapping material 102 may be made of commercially available product from Mitsubishi Rayon Co., Ltd. sold under the trade designation HFE 430-1 Hollow Fiber, which uses polyethylene fibers. Similar wrapping material is also commercially available from Hoechst Celanese Corp. under the designation Heat Exchanger Fiber Mat, which uses polypropylene fibers.

To manufacture the blood heat exchanger, the micro-conduit wrapping material 102 is wrapped about the spindle, the fibers are installed into the shell, and the upper and lower seals are formed by injecting potting compound between the fibers 100 near the upper and lower surfaces of the core. Sufficient potting compound is applied to substantially seal the spaces between the fibers. Then, the fibers 100 are trimmed near each end of the spindle. Preferably, the trimmed fibers 100 form uniform flat upper and lower surfaces of the core. With the seals in place, liquids such as aqueous priming solution and blood may be directed into the fibers 100 through their ends, without leaking any liquid into the spaces between the fibers. Finally, the manifolds are attached to the shell. Also, hoses and other plumbing lines are attached to the heat exchanger 300 as needed, for transportation of heat exchange medium, blood, priming solution, oxygen, and other media as appropriate.

Generally, the heat exchanger regulates the temperature of a patient's blood during a medical procedure such as open heart surgery. Due to the large number of fibers 100 and the small size of the fibers, there is a substantial area of surface contact between the heat exchange medium and the contents of the fibers 100. The temperature of blood flowing through the core is efficiently regulated, due to the high degree of contact between the blood and the heat exchange medium.

The configuration of the lower venous gas header 16, the inner heat exchanger housing 20, the water inlet and outlet nozzles 38 and 40 and the gas mixture outlet nozzle 46, are illustrated in FIGS. 13–17. These parts, along with the raised annular wall member 68 that receives the blood inlet manifold 18, are all injection molded as a single unitary piece of plastic. The inner heat exchanger housing 20 is formed with an interior vertical wall member 76 (FIG. 15) that defines a water flow channel or path 78 (FIGS. 13 and 15) which extends vertically along one side of the heat exchanger housing 20. The lower end of the water flow path 78 communicates with the interior of the water inlet nozzle 38. The upper end of the water flow path 78 communicates through a port 80 (FIG. 15) into the upper interior of the housing 20. This permits the incoming heat exchange water to be disbursed around the upper ends of the thousands of micro-conduits or fibers 50 of the heat exchanger fiber bundle 26. As previously explained, this water flows down around the outside of the fibers 50, through another port 82, and then out through water outlet nozzle 40. The opening of the nozzle 40 is shown at 84 in FIG. 15.

Figure 17:
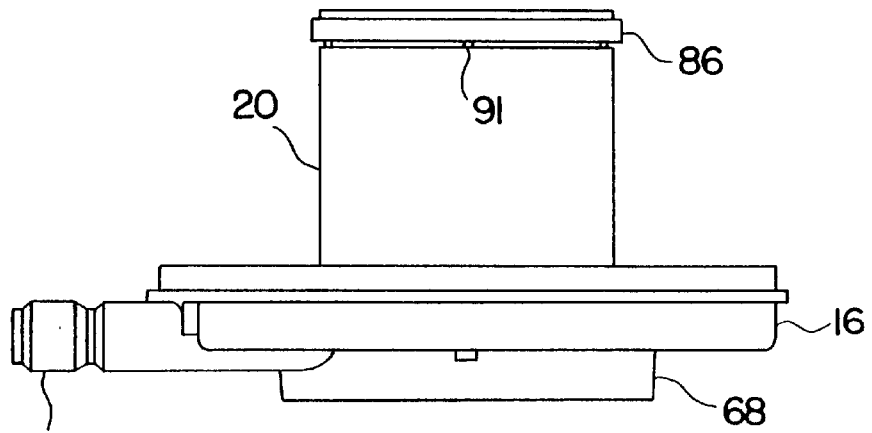
FIG. 17 is a side elevation view of the lower venous gas header and inner heat exchanger housing of the blood oxygenator.
Figure 18:
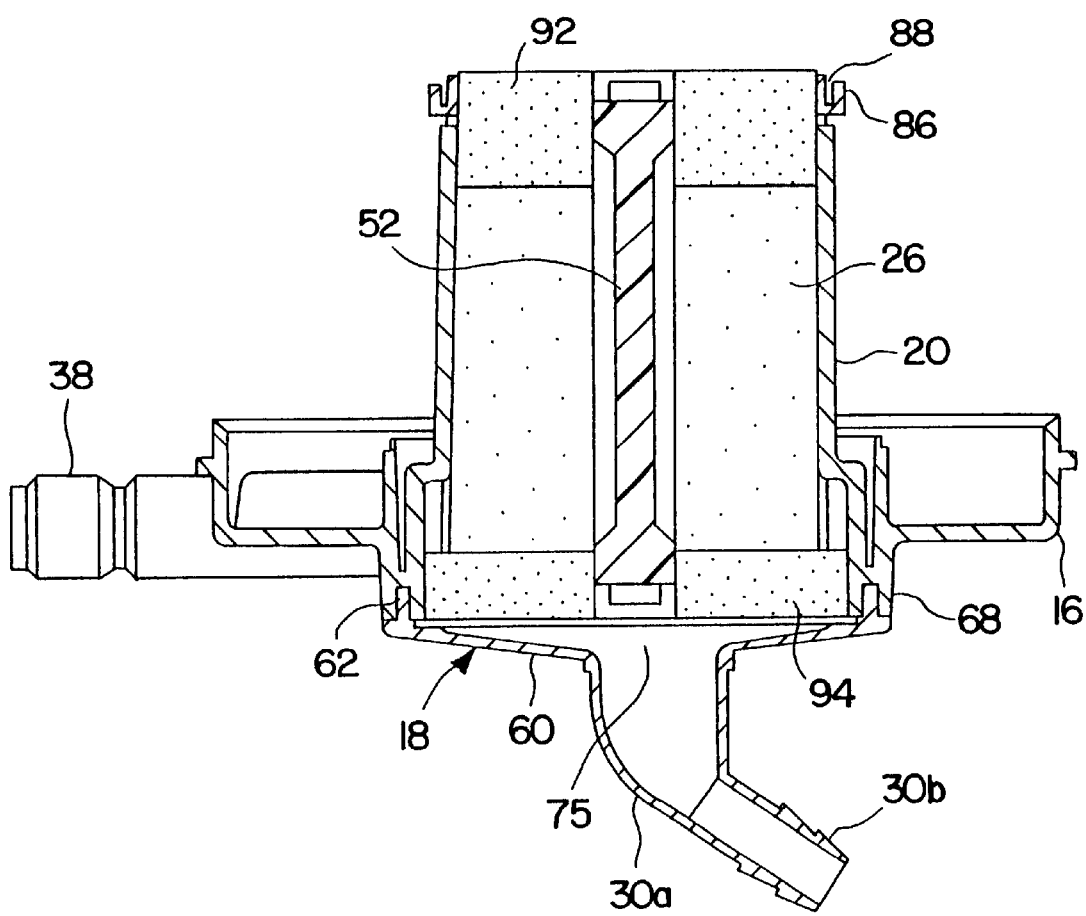
FIG. 18 is an enlarged vertical sectional view of the lower venous gas header and the inner heat exchanger housing with the blood inlet manifold connected. Also illustrated in this view is the micro-conduit fiber bundle of the heat exchanger.

The upper end of the cylindrical heat exchanger housing 20 is molded with a fitting ring 86 (FIGS. 15 and 17) having an upwardly opening circular recess 88 (FIG. 18) for receiving, and interfitting with, a downwardly extending circular flange of the outer heat exchanger housing 22. The fitting ring 86 is connected to the main part of the housing 20 by small plastic extensions 91 (FIG. 17).

Except for the fiber bundles 26 and 28, and the potting compound comprising the seals 92, 94, 106 and 108, the remainder of the structures illustrated and described herein are preferably injection molded of clear polycarbonate plastic. Suitable plastics are sold under the trade designation MAKROLON from Bayer and the trade designation LEXAN HP2R-1112 from General Electric. The separately molded plastic components may be assembled and permanently affixed to each other with a suitable non-toxic ultraviolet (UV) curable adhesive.

Figure 19:
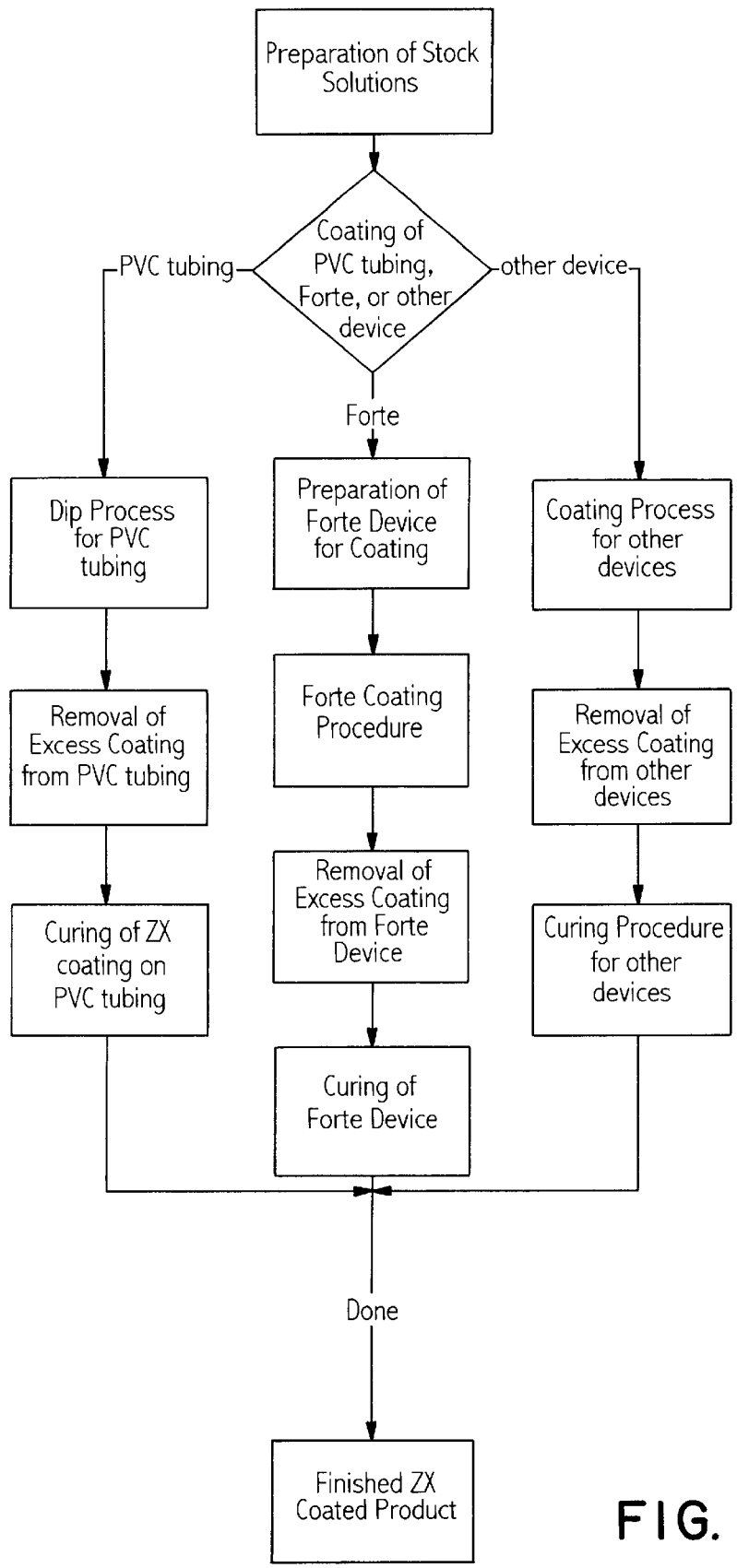
FIG. 19 is a flowchart showing the process steps of a protocol for practicing an embodiment of the invention.

The practice of the invention may illustrated by the following protocol, which should be read in conjunction with the flowchart of FIG. 19. This protocol covers siloxane coating of PVC tubing, oxygenators (using the oxygenators sold under the trade designation MAXIMA FORTÉ from Medtronic as a non-limiting example), and other medical devices.

The required process equipment includes: adequately vented fume hood; roller or centrifugal pump capable of pumping a minimum of 2 liters/minute; constant temperature water bath (sold under the trade designation of LINDBERG/BLUE M or equivalent); stir-plate (sold under the trade designation of BIBBY B212 or equivalent); stir bars; 4000-ml to 6000-ml glass flasks; Viton brand tubing; balance (sold under the trade designation of METTLER 4000 or equivalent); pH meter; 2000-ml to 6000-ml glass volumetric flasks; 500-ml to 2000-ml graduated cylinders; polypropylene and glass funnels; polypropylene and glass containers; aluminum foil; lint-free paper towels; and PVC tubing or equivalent.

The required process materials are: hexanes (ACS Reagent Grade); deionized water ("DI"); aminoalkylsiloxane sold under the trade designation MDX4-4159 from Dow Corning; 0.1-N Glacial acetic acid; IPA; and 1.0-N hydrochloric acid.

Safety glasses and protective gloves should be worn at all times. All operations should be performed in a well vented fume hood. All waste chemicals/solvents should be disposed in appropriate waste containers.

Stock solutions (defined as solutions that have a defined shelf-life which allows preparation before initiating the actual process) should be prepared as follows.

Preparation of IPA premix: combine 75.0-g (74.6-wt %) of IPA, 25.0-g (24.9-wt %) of DI, and 0.5-g (00.5-wt %) of 1.0-N HCl. The solution should be covered immediately and allowed to stir for a minimum of 5 minutes. The IPA premix should be stored at ambient temperature in a tightly closed container free from moisture.

Preparation of aminoalkylsiloxane ("ZX") solids solution may be performed according to either of two options. In the first option, a 3-wt % mixture of ZX solids solution in hexane is formed by combining 1880.0-g (94-wt %) of Hexane and 120.0-g (6-wt %) of the aminoalkylsiloxane sold under the trade designation of MDX4-4159 from Dow Corning. In the second option, a 1.5-wt % ZX solids solution in a IPA/hexane mixture is formed by combining 1580.0-g (79-wt %) of IPA, 360.0-g (18-wt %) of hexane, and 60.0-g (3-wt %) of the aminoalkylsiloxane sold under the trade designation of MDX4-4159 from Dow Corning.

Mixing of the IPA premix and ZX solids solution may also be performed according to either of two options. In the first option, mixing of the IPA premix and 3-wt % ZX solids in hexane is performed by combining 2000.0-g (99-wt %) of 3-wt % ZX solids solution and 20.0-g (1-wt %) of IPA premix. In the second option, mixing of the IPA premix and 1.5-wt % ZX solids in IPA/hexane is performed by combining 2000.0-g (99.5-wt %) of 1.5-wt % ZX solids solution and 10.0-g (0.5-wt %) of IPA premix. The solution should be covered immediately and allowed to stir for a minimum of 5 minutes. The ZX solution should be stored at ambient temperature in a tightly closed container free from moisture.

The ZX coating procedure for PVC tubing involves dipping the tubing in the container of ZX solution for 2 minutes and then removing the tubing from the solution. Removal of excess coating from PVC tubing is performed by allowing excess ZX solution to gravity drain for 1 minute. Then, supply 3 PSI (5–6 SCFM) for 2 minutes, followed by 10 PSI (7–8 SCFM) for 10 minutes. Curing of the ZX coating on the PVC tubing is performed with humid air (50±5% relative humidity) at less than 3 PSI for 30 minutes, followed by 60 minutes of 5–8 PSI of dry air (0% relative humidity).

The coating procedure for microporous hollow fiber membrane oxygenators may be illustrated with the following procedure, which uses, as an example only, the oxygenator sold under the trade designation of MAXIMA FORTÉ by Medtronic. The procedure is easily adapted to other oxygenators using microporous hollow fiber membranes, such as the oxygenator sold under the trade designation of AFFINITY by Medtronic, according to principles known in the art.

To prepare the device for coating, plug two exhaust air ports using any appropriate technique, along with the outlet air port. Position the device in its upright position. The oxygenator must be properly grounded to insure that any static buildup is properly discharged. This can be accomplished by connecting a lead from the thermocouple connector to the micropump. Using a micropump and Viton brand tubing, connect the inlet of the pump to a container of ZX solution and the outlet of the pump to the blood inlet connection of the device. Using Viton brand tubing and the appropriate connections, connect both the recirculation port and blood outlet to the container of ZX solution, thus allowing recirculation of the ZX solution. Connect an air line capable of supplying 1 PSI (8 LPM) to the inlet gas port. Have an air line capable of supplying 3 to 10 PSI (5 to 8 SCFM) to the blood inlet port, which will be used for excess ZX removal.

To coat the device, supply air to the inlet gas port at less than 1 PSI (6 LPM). Turn the micropump on full power for two minutes. After the micropump is turned off, continue to supply air to the inlet gas port at (6 LPM).

To remove excess coating from the device, allow the device to gravity drain for 1 minute. For the next two minutes, continue to supply air to the inlet gas port at less than 1 PSI (6 LPM) and supply 3 PSI (5–6 SCFM) to the blood outlet and recirculation port. After the two minute period, supply 1 PSI (8 LPM) to the inlet gas port and 10 PSI (7–8 SCFM) to the blood outlet and recirculation port for 10 minutes.

To cure the device, use humid air (50±5% relative humidity) at less than 3 PSI for 30 minutes, and then use 5–8 PSI of dry air (0% relative humidity) for 60 minutes.

As for other medical devices, appropriate coating process steps and parameters should take into consideration geometry differences. The curing procedure involves using humid air (50±5% relative humidity) at less than 3 PSI for 30 minutes and then 5–8 PSI of dry air (0% relative humidity) for 60 minutes.

The success of the invention may be demonstrated by considering the following data. Twelve identical oxygenators sold under the trade designation of MAXIMA FORTÉ by Medtronic were tested for plasma breakthrough under identical conditions. The oxygenators were considered and tested in six pairs. One member of each pair of oxygenators was coated with aminoalkylsiloxane compound according to the protocol described above. The other member was uncoated. The test measured the time in hours for confirmed plasma breakthrough.

Results appear below.

| Test Devices | | Control Devices | |
|---|---|---|---|
| Identifier | Time | Identifier | Time |
| T1 97324804 | 72 | C1 | 29 |
| T2 97324483 | 34 | C2 | 26 |
| T3 97324458 | 74 | C3 | 25 |
| T4 97324474 | 54 | C4 | 14 |
| T5 97324467 | 36 | C5 | 22 |
| T6 97324753 | 54 | C6 | 23 |
| Mean | 54 | Mean | 23 |
| Standard Deviation | 16 | Standard Deviation | 5 |

The tests of units T2 and T5 were terminated after 34 and 36 hours, respectively, because of excessive inlet pressure (>1000 mmHG) buildup. This type of pressure increase is common due to the aging of the test fluid (bovine blood) during the study and is not reflective of the performance of the coating. The test of unit C4 was terminated after 14 hours after the microporous fiber developed a leak, which interfered with effluent specific gravity measurements.

Using standard t-Test calculations for two samples (assuming unequal variances), the following results were obtained.

|                              | Variable 1  | Variable 2  |
|------------------------------|-------------|-------------|
| Mean                         | 54          | 23.16666667 |
| Variance                     | 289.6       | 26.16666667 |
| Observations                 | 6           | 6           |
| Hypothesized Mean Difference | 0           |             |
| df                           | 6           |             |
| t Stat                       | 4.250235182 |             |
| P(T $\leq$ t) one-tail       | 0.002689373 |             |
| t Critical one tail          | 1.943180905 |             |
| P(T $\leq$ t) two-tail       | 0.005378746 |             |
| t Critical two tail          | 2.446913641 |             |

Based on a criterion of $p<0.01$, the conclusion was that coating the microporous hollow fiber membranes with an aminoalkylsiloxane compound to reduce migration of plasma across the micropores produced large and statistically significant improvement in plasma breakthrough time.

I claim:

1. A medical device comprising a hollow fiber membrane comprising micropores and a siloxane copolymer coating on the hollow fiber membrane that does not cover or fill the micropores, wherein the siloxane copolymer coating presents a surface near the micropores that reduces the migration of plasma across the micropores in the membrane.

2. The device of claim 1 where the copolymer comprises aminoalkylsiloxane.

3. The device of claim 2 where the aminoalkylsiloxane comprises a solution containing active aminofunctional dimethylsiloxane copolymer and at least one aliphatic solvent and at least one isopropanol solvent.

4. The device of claim 1 in which the siloxane copolymer coating is applied to the hollow fiber membrane by:

formulating a liquid siloxane copolymer coating; and coating the device to create a thin film of silicone on the hollow fiber membrane, where the copolymer coating neither covers or fills the micropores; and curing the copolymer coating on the device.

5. A medical device comprising a microporous hollow fiber membrane, in which the membrane is coated with an alkoxysilane/alkylsilane copolymer coating by a method comprising the steps of:

formulating a liquid alkoxysilane/alkylsilane copolymer coating; and coating the device to create a thin film of silicone on the microporous fiber membrane to the extent sufficient to reduce migration of plasma across micropores in the membrane but neither covering or filling any micropores, and curing the copolymer on the device.

6. A medical device comprising a microporous hollow fiber membrane having a coating applied to the membrane according to a method comprising the steps of:

formulating a liquid alkoxysilane/alkylsilane copolymer coating; and coating the device to create a thin film of silicone on the microporous fiber membrane but neither covering or filling any micropores, and curing the copolymer on the device.

7. The device of claim 6, in which the coating increases resistance to plasma breakthrough in the device by changing the surface of the microporous fiber membrane near micropore openings.

8. The device of claim 7, in which the copolymer comprises aminoalkylsiloxane.

9. The device of claim 8, in which the aminoalkylsiloxane comprises a solution containing active aminofunctional dimethylsiloxane copolymer and at least one aliphatic solvent and at least one isopropanol solvent.

10. The device of claim 6, in which the copolymer comprises aminoalkylsiloxane.

11. The device of claim 10, in which the aminoalkylsiloxane comprises a solution containing active aminofunctional dimethylsiloxane copolymer and at least one aliphatic solvent and at least one isopropanol solvent.

* * * * *

UNITED STATES PATENT AND TRADEMARK OFFICE
CERTIFICATE OF CORRECTION

PATENT NO. : 6,395,226 B1  Page 1 of 1
DATED : May 28, 2002
INVENTOR(S) : Plunkett It is certified that error appears in the above-identified patent and that said Letters Patent is hereby corrected as shown below:

Title page,
Item [54], Title, change "ALKOXYSILANE/AKLYSILANE" to
-- ALKOXYSILANE/ALKYLSILANE --.

Column 12,
Line 8, change "membrane to the extent" to -- membrane to an extent --.

Signed and Sealed this

Twenty-second Day of June, 2004

JON W. DUDAS
*Acting Director of the United States Patent and Trademark Office*